United States Patent [19]
Baxter et al.

[11] Patent Number: 5,831,183
[45] Date of Patent: Nov. 3, 1998

[54] INTEGRATED STACK GAS SAMPLER

[75] Inventors: Robert Baxter, Raleigh; Daniel Ealy, Youngsville; Derrick Hinkle, Louisburg, all of N.C.

[73] Assignee: B3 Systems, Inc.

[21] Appl. No.: 869,620

[22] Filed: Jun. 5, 1997

[51] Int. Cl.⁶ ........................................ G01N 1/00
[52] U.S. Cl. ........................................ 73/563.51
[58] Field of Search ............... 73/863.33, 863.41, 73/863.43–863.45, 863.51–863.58, 863.71, 863.81, 864.81; 374/147, 148; 137/599

[56] References Cited

U.S. PATENT DOCUMENTS

| | | |
|---|---|---|
| 3,005,347 | 10/1961 | Smithson . |
| 3,459,047 | 8/1969 | Sumansky . |
| 3,672,206 | 6/1972 | Goto ........................................ 374/148 |
| 3,783,695 | 1/1974 | Grothe et al. ........................ 73/863.56 |
| 3,937,248 | 2/1976 | Hutton .................................. 137/599 |
| 4,840,074 | 6/1989 | Jessop ................................. 73/863.56 |
| 4,860,598 | 8/1989 | Bailey et al. ........................ 73/863.33 |
| 4,946,650 | 8/1990 | Rothele ............................... 73/863.56 |
| 5,302,026 | 4/1994 | Phillips ................................ 374/148 |

FOREIGN PATENT DOCUMENTS

| | | | |
|---|---|---|---|
| 2 315 072 | 10/1974 | Germany . | |
| 781180 | 12/1978 | U.S.S.R. . | |
| 0842458 | 6/1981 | U.S.S.R. ........................... | 73/863.56 |

Primary Examiner—Robert Raevis
Attorney, Agent, or Firm—Myers Bigel Sibley & Sajovec

[57] ABSTRACT

The present invention provides a sampling apparatus for taking a representative gas sample from a flowing gas stream. The sampling apparatus can be positioned within a conduit carrying a gas stream, such as a gas line or smoke stack. Preferably, the sampling apparatus comprises a cylindrical collection tube having collection wings radially projecting therefrom. It is further preferred that the bottom edges of the collection wings contain at least one elongate collection opening, through which a representative gas sample enters the sampling apparatus. In particular embodiments of the invention, the sampling apparatus further comprises an electronic sensor positioned within the collection tube. Alternatively, the sensing device is located at a site remote from the collection tube and is connected thereto by a connecting hose.

20 Claims, 4 Drawing Sheets

INTEGRATED STACK GAS SAMPLER

FIELD OF THE INVENTION

The present invention relates to an apparatus for taking a representative gas sample, in particular an apparatus for inserting into a gas line or smoke stack for taking a representative sample from a gas stream flowing therein.

BACKGROUND OF THE INVENTION

The analysis of gaseous compounds and particulate matter emitted from smoke stacks, gas lines, and other industrial sources is necessary for compliance with environmental regulations and improved process control. To achieve an accurate assessment of industrial emissions or gas concentrations, it is desirable that the sample removed from the gas stream for analysis be representative of the total gas stream. There have been previous efforts to devise apparatus for taking a representative sample from a flowing stream.

U.S. Pat. No. 3,005,347 discloses an apparatus for sampling solid materials, such as ores, animal feed, and fertilizers, flowing downward through a vertical chute. The apparatus has a single sample inlet slot through which the solid material enters and flows into a hollow bifurcated sampling arm, with the hollow legs of the bifurcated sampling arm pivotally mounted on a hub assembly. The sample inlet slot is approximately perpendicular to the flow of the solid material, and traverses most of the width of the chute. The apparatus further includes a pivot for moving the sampling arm so that the sample inlet slot travels in an arc through the stream of flowing material. The sampled material flows through the hollow legs of the bifurcated sampling arm and exits the apparatus, at which point the sampled material can be subjected to analysis.

U.S. Pat. No. 3,459,047 discloses a probe for inserting into a gas main to sample gases flowing therein. The gas sampling probe contains an elongated sampling tube with at least one hole therein. The tip of the glass tube within the gas main is closed, and the other end, lying outside the gas main, is open and leads to an analyzer. Gases enter the sampling tube through the hole(s) therein, and then flow outward to the analyzer. The sampling tube is partially surrounded by a horse-shoe shaped sheath. The sheath also contains fluid inlet and outlet tubes, which permit the sheath to be heated or cooled. The probe is aligned within the gas main so that it lies perpendicular to the gas flow, and the hole(s) in the sampling tube is facing upstream relative to the gas flow, and the opening in the sheath is facing downstream relative to the gas flow. The sheath is designed to allow gas to enter the sampling tube while preventing particulate matter suspended in the gas stream from contacting the sampling tube, thereby clogging up the sampling tube or the holes therein.

U.S. Pat. No. 4,860,598 discloses a device for taking a representative sample of air from a laminar flow air stream to determine the number of particles therein. One embodiment of the device is a planar gridwork structure with a central hollow tube and a plurality of smaller hollow tubes extending laterally therefrom. The smaller lateral tubes contain regularly spaced holes for gas samples to enter. The device is oriented perpendicularly to the air stream flow, and is sized so as to minimize disruption of the path of the air stream. All of the holes draw equally from the air stream, so that a representative sample is taken therefrom. Only one end of the central tube is open. The gas sample passes through the single opening in the central tube to a discharge tube leading to an analytical device for determining particle number in the gas sample. In an alternate embodiment, the planar gridwork consists of interconnected hollow circular tubes with regularly spaced holes therein.

German Patent No. 2,315,072 discloses a device for taking samples from a non-homogeneous medium, for example, wet steam. The device is comprised of a manifold, the arms of which contain hollow radial tubes through which the sample flows. Projecting from the arms of the manifold and connecting to the tubes therein are a plurality of probes. The entire apparatus is integrated into the flow channel, and the radial tubes within the manifold appear to connect to discharge tubes leading out of the manifold through the wall of the flow channel. The outermost probe on each arm of the manifold lies against the inner wall of the flow channel and has side-openings that appear to connect with the discharge tubes leading out of the manifold. The manifold lies perpendicular to the flow stream, and the probes project out into the flow stream. The samples enter the probes, flow into the radial tubes within the manifold, then flow in an outward direction and exit the manifold through the discharge tubes leading out through the wall of the flow channel.

Soviet Union Patent No. 781,180 discloses a hydrometallurgical pulp sampler. The apparatus contains a star-shaped collecting rod, comprising 4–8 hollow perforated tubes. The collecting rod is oriented perpendicular to the flow of the pulp stream. Samples enter the apparatus through the perforations in the collecting rod, flow downward to the lower ends of the multiple arms of the collecting rod, and are then pooled and exit the pulp line through a single sample discharging line in a direction perpendicular to the pulp stream flow. The collecting rod is attached to the lower end of a conical turbuliser. The turbulising cone has spiral ribs and functions by disrupting the flow of the pulp stream. At the tip of the turbulising cone is a solid star-shaped supporting device. The apparatus is integrated within a pulp line, and is situated so that the support star lies upstream, and the base of the turbulising cone and the collecting arm lie downstream relative to the flow of the pulp stream.

There remains a need in the art for apparatus that can be inserted into a conduit carrying a gas stream, such as a gas line or smoke stack, and take a representative sample from a gas stream flowing therein.

SUMMARY OF THE INVENTION

The present invention is directed toward a sampler configured to be inserted into a conduit, such as a gas line, smoke stack, or other process line.

A first aspect of the present invention is an apparatus for taking a sample from a gas stream flowing within a conduit. The apparatus comprises an elongate collection tube having a closed upstream portion, a central portion, and a downstream portion, with the downstream portion having an exhaust opening formed therein. A plurality of collection wings are connected to the collection tube central portion and project radially outward therefrom, with each of the collection wings having an outer edge portion and an upstream edge portion. The collection wing outer edge portions are configured to contact the conduit so that the collection tube is positioned within the conduit generally parallel to the flow of the gas stream. Each of the upstream edge portions have at least one collection opening formed therein, with each of the collection openings being in fluid communication with the exhaust opening.

A second aspect of the present invention is a system for collecting a sample from a gas stream. The system comprises a conduit configured for containing a gas stream, with the conduit having an inner wall. An elongate collection tube is positioned within the conduit. The collection tube has a closed upstream portion, a central portion, and a downstream portion, with the downstream portion having an exhaust opening formed therein. A plurality of collection wings are connected to the collection tube central portion and project radially outward therefrom, with each of the collection wings having an outer edge portion and an upstream edge portion. The collection wing outer edge portions contact the conduit inner wall so that the collection tube is positioned within the conduit generally parallel to the flow of the gas stream therein. Each of the upstream edge portions have at least one collection opening formed therein, with each of the collection openings being in fluid communication with the exhaust opening. Sampling means for collecting a sample from the gas stream are positioned within the collection tube downstream portion.

The foregoing and other aspects of the present invention are described in more detail in the detailed description set forth below.

DETAILED DESCRIPTION OF THE PREFERRED EMBODIMENTS OF THE INVENTION

The invention disclosed herein provides a sampling apparatus for taking a representative gas sample from a flowing gas stream. In particular, provided herein is a sampling apparatus configured to be inserted into a conduit carrying a gas stream, such as a gas line, smoke stack, or other process line. The sampler may be fabricated from any suitable material depending upon the particular environment for which it is intended for use (e.g., stainless steel).

Figure 1:
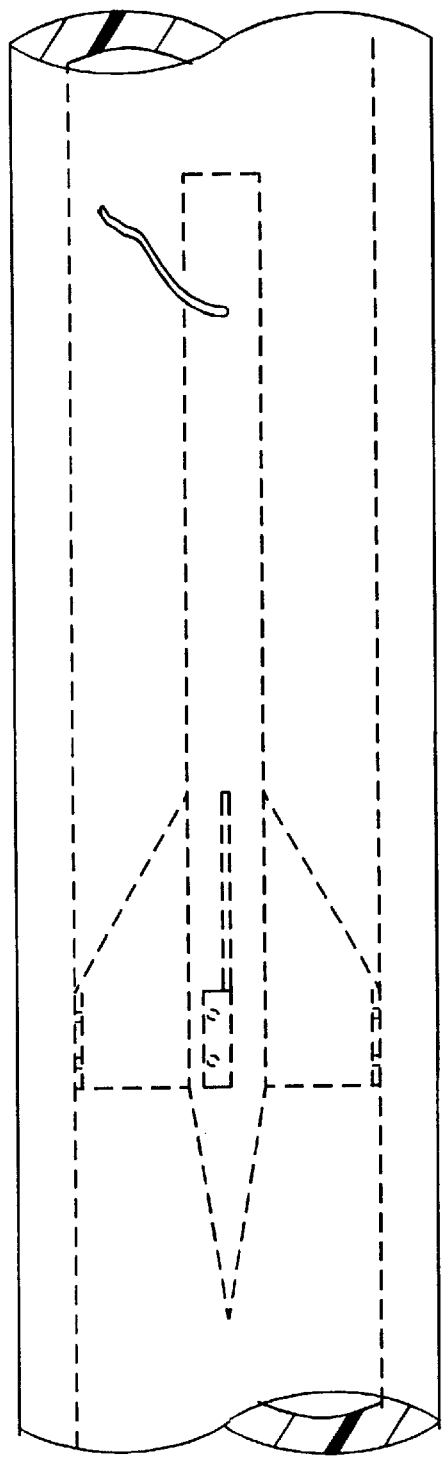
FIG. 1 is a side sectional view of a conduit with the sampling apparatus inserted therein.
Figure 2:
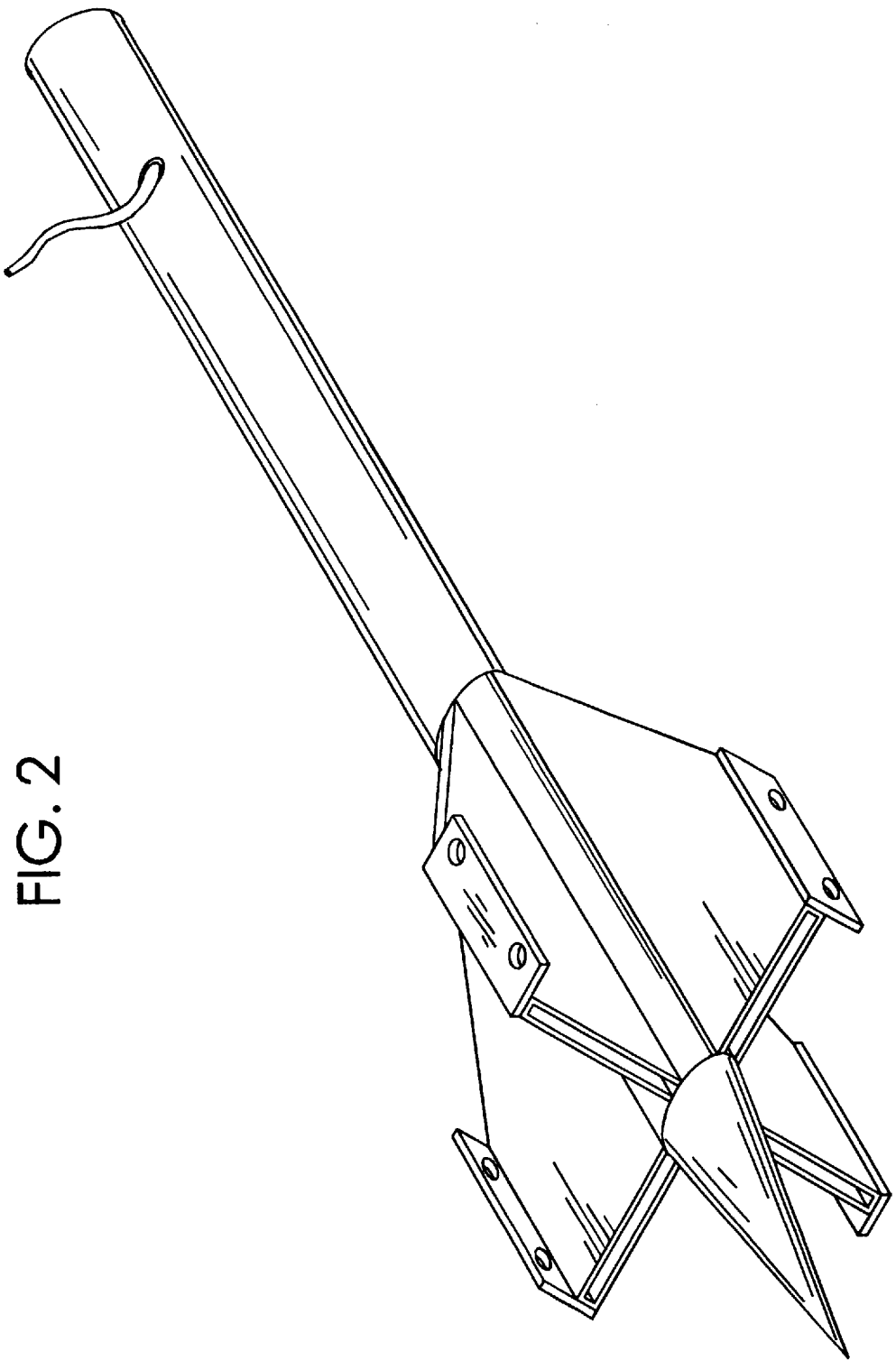
FIG. 2 is a perspective view of the outer surface of the sampling apparatus of FIG. 1.

Turning to FIGS. 1–2, the sampling apparatus 10 contains a collection tube 20, the collection tube 20 being divided generally into three sections: a downstream section, a central section, and an upstream section. The collection tube 20 is preferably elongate, more preferably cylindrical, in shape. The upstream end 21 of the collection tube 20 is closed, and the downstream section has an exhaust opening 22 formed therein. A plurality of collection wings 30 are connected to the central section of the collection tube 20 and project radially outward therefrom. Each of the collection wings 30 has two edges: an outer edge 32 and a bottom (i.e., upstream) edge 31. The bottom edge 31 of each collection wing 30 has at least one collection opening 33 formed therein. The collection openings 33 are in fluid communication with the exhaust opening 22 formed in the downstream section of the collection tube 20.

The sampling apparatus 10 has at least one, preferably at least two, collection wings 30 radiating outward from the central section of the collection tube 20. There are no particular upper or lower limits to the number of collection wings 30, with apparatus having two, three, four, five, six, eight and ten collection wings 30 being preferred, and apparatus having three or four collection wings 30 being most preferred. The bottom edge 31 of each collection wing 30 has at least one collection opening 33 formed therein, through which a representative gas sample can be taken from the flowing gas stream. Preferably, the collection opening 33 is an elongate slot. A grill may be provided over the slot if desired. There are no particular upper or lower limits to the number of collection openings 33 in the bottom edge 31 of each collection wing 30, as long as a representative sample is taken from the gas stream. Collection wings 30 having one, two, three, four, or six collection openings 33 in the bottom edges 31 thereof are preferred.

As shown in FIG. 1, the sampling apparatus 10 is designed to be inserted into a conduit 50 configured to contain a gas stream. The conduit 50 has an outer wall 51 and an inner wall 52. The sampling apparatus 10 is mounted to the inner wall 52 of the conduit 50 by at least one bracket mount 40 that screws into the inner wall 52 of the conduit 50. The mounts 40 are connected to the sampling apparatus 10 at the outer edge 32 of at least one of the collection wings 30, and the entire sampling apparatus 10 is thereby mounted to the inner wall 52 of the conduit 50. Mounts 40 may be connected to one, two, three or more of the collection wings 30. Numerous alternatives to such bracket mounts are available for different conduit constructions. These alternatives will be readily apparent to those skilled in the art, and include couplings, suspension cables, refractory brick mounts, welding, interlocking brackets, and cam-locks.

The sampling apparatus 10 is positioned within the conduit 50 so that the collection tube 20 lies generally parallel to the flow of the gas stream within the conduit 50 (the gas flow is indicated in FIG. 1 by an arrow). The bottom edges 31 of the collection wings 30 are positioned to lie perpendicular to the flow of the gas stream. The collection openings 33 formed in the bottom edges 31 of the collection wings 30 open upstream into the flow of the gas stream.

Figure 3:
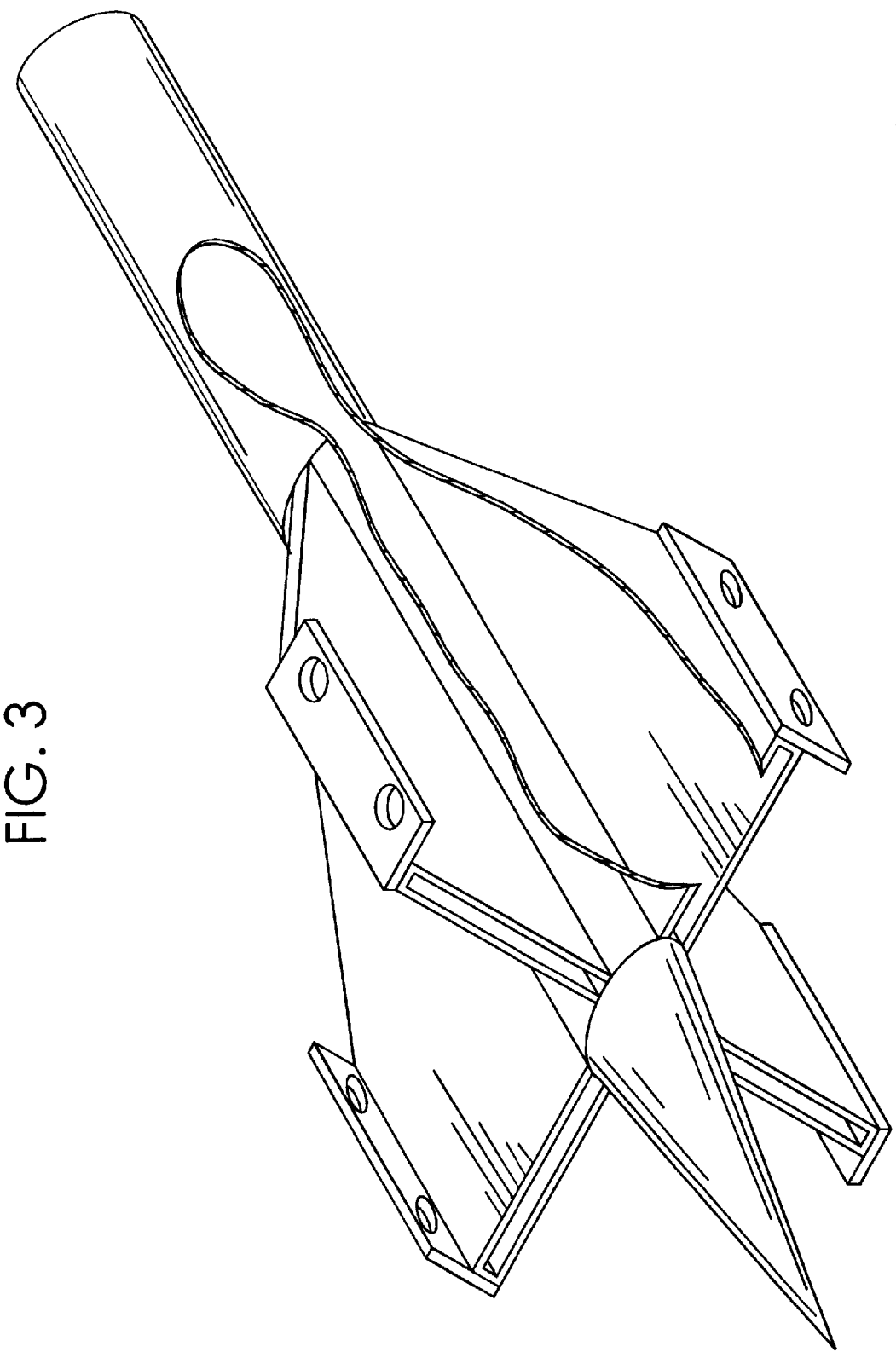
FIG. 3 is a partial cut-away perspective of a sampling apparatus of the invention cut off along the downstream portion of the collection tube.

FIG. 3 presents the downstream and central sections of the collection tube 20 and collection wings 30 in a partial cut-away perspective. The gas sample enters the sampling apparatus 10 through the collection openings 33 in the bottom edges 31 of the collection wings 30. The interior space 60 of the collection wings 30 are in fluid communication with the interior space 61 of the collection tube 20 and the exhaust opening 22 formed in the downstream section thereof. Thus, the sample flows from the collection openings 33 into the interior space 60 of the collection wings 30, and from there enters the interior space 61 of the collection tube 20, moving in a downstream direction therein. In the embodiment of the invention shown in FIG. 4, the bulk of the gas sample exits the sampling apparatus 10 through the exhaust opening 22 in the downstream section of the collection tube 20 and re-enters the gas stream.

In preferred embodiments of the invention, shown in FIGS. 1–4, a sampling probe 42 is positioned within the downstream section of the collection tube 20. The sampling probe 42 is connected to the interior wall 23 of the collection tube 20 by a mounting device 64, such as a bracket. In one preferred embodiment of the invention, shown in FIG. 4, the sampling probe 42 is a connecting hose, which leads out of the collection tube 20 through an opening 41 in the wall thereof and connects with a remote electronic sensor. According to this embodiment, a small portion of the representative gas sample in the collection tube 20 is re-sampled by the connecting hose 42 and is analyzed by a remote electronic sensor, such as a particle detector, gas analyzer or temperature-sensing device. The rest of the representative gas sample exits the collection tube 20 through the exhaust opening 22 formed in the downstream section thereof. In an alternate preferred embodiment, the sampling probe 42 is an electronic sensor, such as a particle detector, gas analyzer, or temperature-sensing device. According to this embodiment, the electronic sensor is positioned within the downstream section of the collection tube 20, and all of the representative gas sample exits the collection tube 20 through the exhaust opening 22.

In yet another preferred embodiment, the down-stream end of the collection tube 20 is closed off (i.e., with no exhaust opening 22 formed therein), and all of the representative gas sample exits the collection tube 20 by way of a connecting hose 42 attached to a remote electronic sensor, defined as above.

Figure 4:
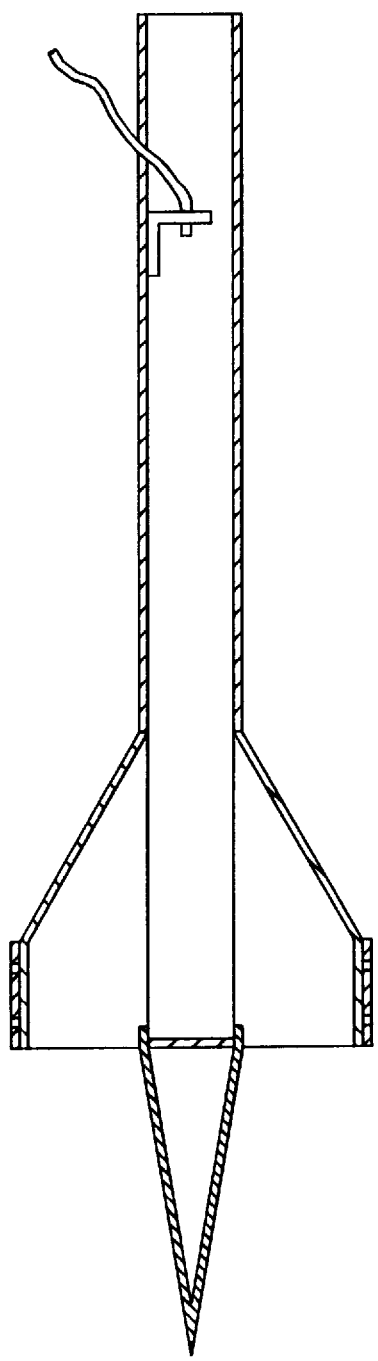
FIG. 4 is a side sectional view of the sampling apparatus of FIG. 1, showing the sampling probe mounted to the interior wall of the collection tube by an L-shaped bracket.

The sampling apparatus 10 removes a representative gas sample from a gas stream. In one preferred embodiment of the invention shown in FIGS. 1–4, the upstream closed end 21 of the collection tube 20 is tapered or conical in shape so as to minimize the introduction of turbulence into the gas stream caused by the placement of the sampling apparatus 10 into the conduit 50. Turbulence in the gas flow near the collection openings 33 will impair the representative nature of the sample collected from the gas stream. In this particular embodiment of the invention, as shown in FIG. 4, the interior space 62 of the upstream section of the collection tube 20 is not in fluid communication with the interior space 61 of the central or downstream sections of the collection tube 20 and the interior space 60 of the collection wings 30, and is separated therefrom by a partition 63. Preferably, the partition 63 is flat as shown in FIG. 4, or alternatively, an inverted cone. Thus, the gas sample does not enter the interior space 62 of the upstream section of the collection tube 20.

Although the foregoing invention has been described in some detail by way of illustration and example for purposes of clarity and understanding, it will be obvious to one skilled in the art that certain changes and modifications may be practiced within the scope of the appended claims.

That which is claimed:

1. An apparatus for taking a sample from a gas stream flowing within a conduit, said conduit having an inner wall, said apparatus comprising:
   (a) an elongate collection tube having a closed upstream end portion, a central portion, and a downstream portion, said downstream portion having an exhaust opening formed therein, said collection tube configured to define an outer opening between said collection tube and said conduit inner wall along the entire length of said collection tube and in fluid communication with said exhaust opening, through which outer opening said gas stream passes when said apparatus is positioned within said conduit;
   (b) a plurality of collection wings connected to said collection tube central portion and projecting radially outward therefrom, each of said collection wings having an outer edge portion and an upstream edge portion, with said collection wing outer edge portions configured to contact said conduit so that said collection tube is positioned within said conduit generally parallel to the flow of said gas stream, with each of said upstream edge portions having at least one collection opening formed therein, and with each of said collection opening being in fluid communication with said exhaust opening.

2. An apparatus according to claim 1, further comprising sampling means for collection of a sample from said gas stream, said sampling means positioned within said collection tube downstream portion.

3. An apparatus according to claim 1, further comprising means for engaging the internal wall of said conduit connected to at least one of said sampling wing outer edge portions.

4. An apparatus of claim 1 having 3 collection wings.

5. An apparatus of claim 1 having 4 collection wings.

6. An apparatus according to claim 1, wherein said collection tube is a cylindrical tube.

7. An apparatus according to claim 1, wherein said collection tube upstream portion is tapered in shape.

8. An apparatus according to claim 1, wherein said collection tube upstream portion is conical in shape.

9. An apparatus according to claim 2, wherein said sampling means is an electronic sensor.

10. An apparatus according to claim 2, wherein said sampling means is a collection tube.

11. An apparatus according to claim 1, wherein each of said collection opening is an elongate slot.

12. A system for collecting a sample from a gas stream, said system comprising:
   (a) a conduit configured for containing a gas stream, said conduit having an inner wall;
   (b) an elongate collection tube positioned within said conduit, said collection tube having a closed upstream end portion, a central portion, and a downstream portion, said downstream portion having an exhaust opening formed therein, said collection tube configured to define an outer opening between said collection tube and said conduit inner wall along the entire length of said collection tube and in fluid communication with said exhaust opening, through which outer opening said gas stream passes;
   (c) a plurality of collection wings connected to said collection tube central portion and projecting radially outward therefrom, each of said collection wings having an outer edge portion and an upstream edge portion, with said collection wing outer edge portions contacting said conduit inner wall so that said collection tube is positioned within said conduit generally parallel to the flow of said gas stream therein, with each of said upstream edge portions having at least one collection opening formed therein, and with each of said collection openings being in fluid communication with said exhaust opening; and
   (d) sampling means for collecting a sample from said gas stream, said sampling means positioned within said collection tube downstream portion.

13. An apparatus of claim 12 having 3 collection wings.

14. An apparatus of claim 12 having 4 collection wings.

15. An apparatus according to claim 12, wherein said collection tube is a cylindrical tube.

16. An apparatus according to claim 12, wherein said collection tube upstream portion is tapered in shape.

17. An apparatus according to claim 12, wherein said collection tube upstream portion is conical in shape.

18. An apparatus according to claim 12, wherein said sampling means is an electronic sensor.

19. An apparatus according to claim 12, wherein said sampling means is a collection tube.

20. An apparatus according to claim 12, wherein each of said collection openings is an elongate slot.

* * * * *